(12) United States Patent
Robinson et al.

(10) Patent No.: US 10,695,194 B2
(45) Date of Patent: Jun. 30, 2020

(54) INSTRUMENT CONFIGURED TO GENERATE AN IMPACT AND RETRACTING LOAD ON AN INSERTER

(71) Applicant: Alphatec Spine, Inc., Carlsbad, CA (US)

(72) Inventors: Scott Robinson, Encinitas, CA (US); Nathaniel DuBois, Vista, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 754 days.

(21) Appl. No.: 15/360,054

(22) Filed: Nov. 23, 2016

(65) Prior Publication Data

US 2018/0140438 A1    May 24, 2018

(51) Int. Cl.
  *A61F 2/46*    (2006.01)

(52) U.S. Cl.
  CPC ..... *A61F 2/4611* (2013.01); *A61F 2002/4619* (2013.01); *A61F 2002/4627* (2013.01); *A61F 2002/4681* (2013.01)

(58) Field of Classification Search
  CPC ................. A61F 2002/4681; A61F 2002/4627
  See application file for complete search history.

(56) References Cited

U.S. PATENT DOCUMENTS

| 5,788,701 | A  | 8/1998 | McCue |
| 8,696,681 | B2 | 4/2014 | Harris et al. |
| 2006/0178673 | A1 | 8/2006 | Curran |
| 2013/0204265 | A1 | 8/2013 | Capek et al. |

FOREIGN PATENT DOCUMENTS

| WO | 2007098549 A1 | 9/2007 |
| WO | 2014091454 A1 | 6/2014 |

*Primary Examiner* — Andrew Yang
(74) *Attorney, Agent, or Firm* — Honigman LLP (57) ABSTRACT

An instrument and inserter kit for providing a load to insert or retract an implant 2000 is provided. The instrument includes a cover having an engagement end opposite a distal end. The engagement end is configured to mount to an engagement feature of a handle of an inserter. The cover is an elongated member having a C-shaped profile having a dimension configured to receive a sliding member. The sliding member is seated over the cover and is weighted. The sliding member is configured to slide between a first radial lip and a second radial lip so as to provide an impacting force or retracting force on the instrument.

21 Claims, 7 Drawing Sheets

ABSTRACT

INSTRUMENT CONFIGURED TO GENERATE AN IMPACT AND RETRACTING LOAD ON AN INSERTER

FIELD OF THE INVENTION

An instrument configured to attach to an inserter and provide an impact force or retracting force to the inserter is provided.

BACKGROUND OF THE INVENTION

Inserters are currently known and used for introducing an implant between adjacent vertebrae. The inserter includes an end configured to grip the implant. In some instances the muscular load between the adjacent vertebrae makes the insertion of the implant difficult. Accordingly, it is known to use an instrument commonly referred to as a slap hammer to provide an impacting force or in the alternative to provide a retracting force as is needed in a spinal procedure. For instance, the slap hammer may be used to provide an impacting force onto a proximal end of the handle of an inserter so as to drive the implant between the adjacent vertebrae. In some instances where the implant has been driven too far, the slap hammer is provide a retracting force in an opposite direction so as to retract the implant from its inserted position to a predetermined position.

Figures 1A, 1B:
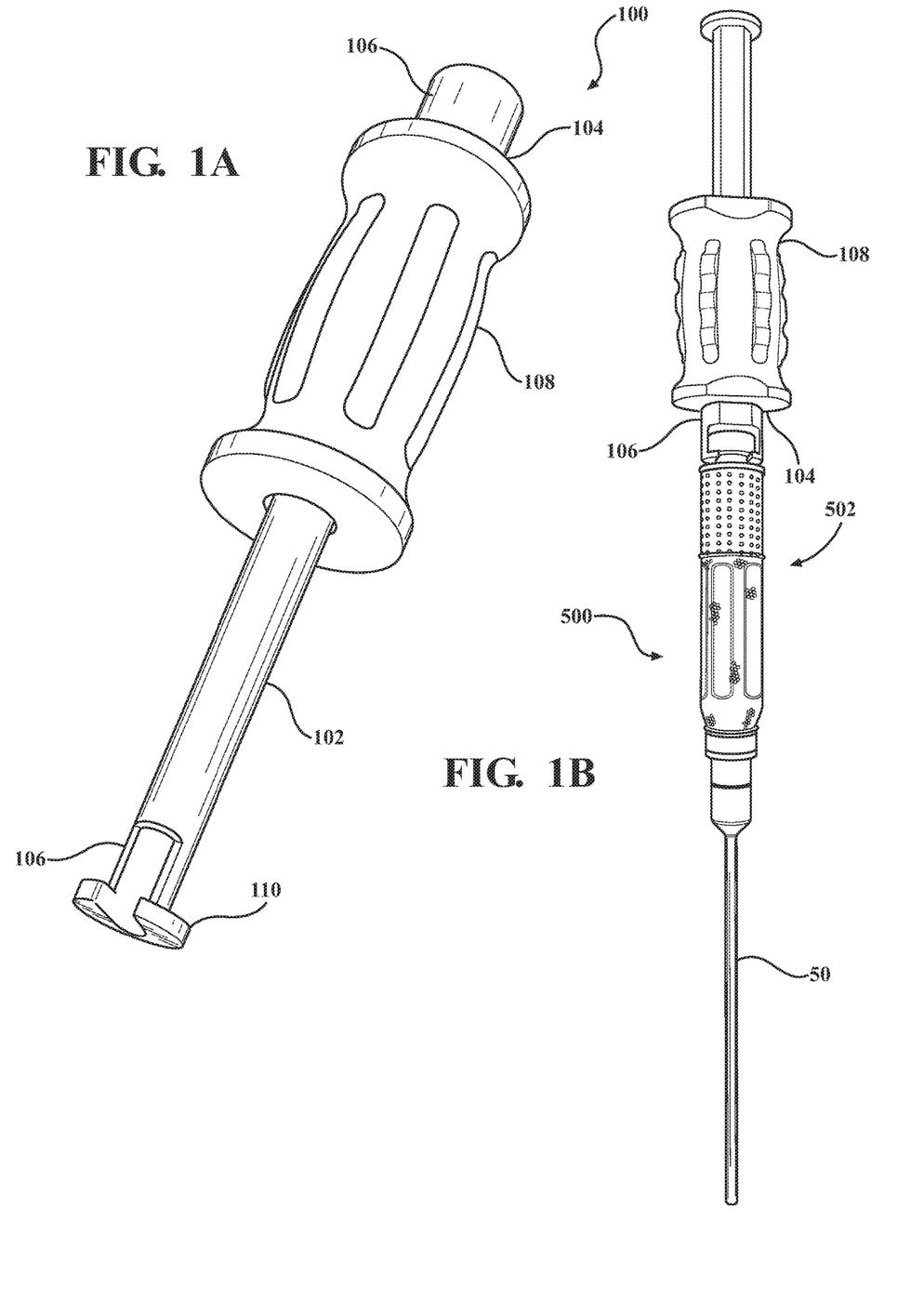
FIG. 1A is an isolated view of a slap hammer of the prior art.
FIG. 1B is a view of the slap hammer shown in FIG. 1A mounted to an inserter.

With reference now to FIGS. 1A and 1B, an illustrative embodiment of a slap hammer 100 currently known and used in the art is provided. The slap hammer 100 is mounted to a distal end of an inserter 500. In particular, the slap hammer 100 is mounted to a handle 502 of the inserter 500. The slap hammer 100 includes a bar 102 having a first radial lip 104 and an engagement feature 106 on a proximal end. The engagement feature 106 is configured to engage a distal end of the handle 502 of the inserter 500. The first radial lip 104 is integrally formed to the engagement feature 106 and provides a surface for which a sliding block 108 may abut against so as to generate an impacting force. A second radial lip 110 is formed on the proximal end of the bar 102 so as to provide a surface for the sliding block to abut against so as to generate a retracting force.

The sliding block 108 is slidably attached to the bar 102 so as to slide between the second radial lip 110 and the first radial lip 104. It should be appreciated that the sliding block 108 may be slid from the second radial lip 110 towards and against the first radial lip 104 to drive the implant (not shown) into the space between adjacent vertebrae whereas when the sliding block 108 is driven towards the second radial lip 110 from the first radial lip 104, a retracting force is generated so as to help pull the implant back. Such an operation may be desired in instances where the implant has been driven too far.

It should be also appreciated that the current slap hammer adds considerable length to the inserter 500 when mounted to the distal end. Accordingly, it may be cumbersome and difficult to use in instances where a surgeon is relatively short. Accordingly, it remains desirable to have a slap hammer configured to minimize the length of the inserter and slap hammer assembly so as to accommodate the use by surgeons of any height.

SUMMARY OF THE INVENTION

An instrument for providing a load to insert or retract an implant is provided. The instrument includes a cover having an engagement end opposite a distal end. The engagement end is configured to mount to an engagement feature of a handle of an inserter. The cover is an elongated member having a C-shaped profile having a dimension configured to receive a sliding member. The sliding member is seated within the cover and is weighted. The sliding member is configured to slide between a first radial lip and a second radial lip so as to provide an impacting force or retracting force on the instrument. Accordingly, the instrument reduces the length of the slap hammer and inserter assembly shown in FIG. 1B.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION OF THE PREFERRED EMBODIMENTS

An instrument for providing an impacting force and a retracting force to an inserter is provided. The instrument includes a cover configured to engage a handle of an inserter. The instrument includes a slide slidably mounted to the cover so as to impact one end of the cover and impart an impacting force onto the instrument so as to insert an implant between adjacent vertebrae or provide a retracting force to an opposite end of the cover so as to provide a retracting force to pull the implant away from the surgical site. The handle of the inserter may be positioned within the cover. Accordingly, the instrument is shorter relative to current slap hammers and thus is not cumbersome and may be used by surgeons of all different heights.

Figure 2:
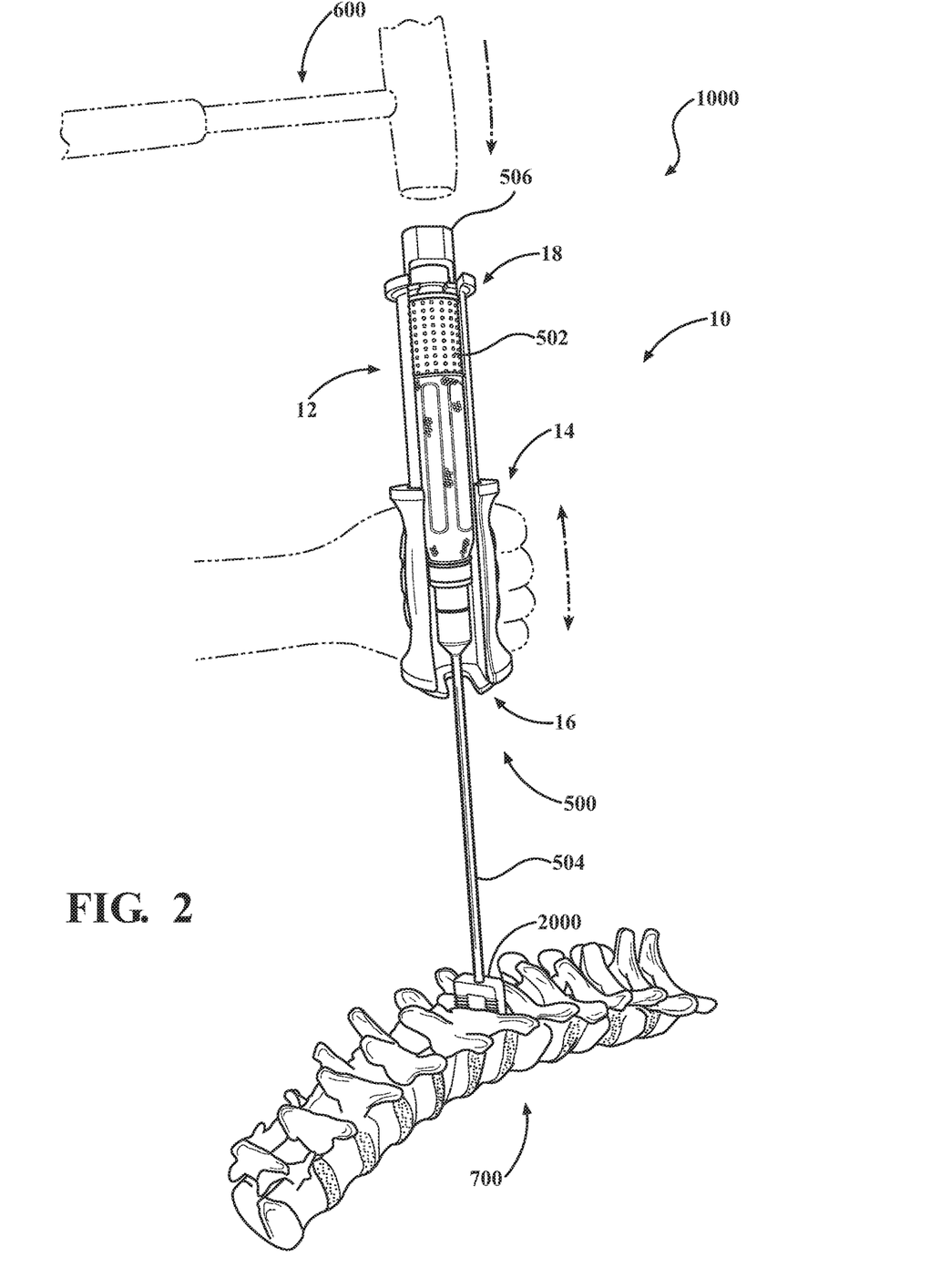
FIG. 2 is a perspective view of an instrument for providing an impacting force and a retracting force to an inserter.

With reference now to FIG. 2, an illustrative view of an instrument 10 for use with an inserter 500 is provided. The inserter 500 includes a handle 502 and an inserting rod 504. The handle 502 may include a hammer support surface 506 extending from the proximal end of the handle 502. The hammer support surface 506 may be integrally formed to the handle 502 and is configured to receive a blow from a hammer 600.

The instrument 10 is configured to provide an impacting or retracting force to advance or pull, as the case may be, an implant 2000 in and out of the surgical site. The instrument 10 is also configured to receive a blow from a hammer 600 to drive the implant 2000 into the surgical site. The instrument 10 may be used to deliver a small impacting force to facilitate a small advancement of the implant 2000 relative to the impacting force delivered by a hammer 600.

The instrument 10 includes a cover 12. The cover 12 is adapted to receive the handle 502 of the inserter 500. A slide 14 is slidably mounted to the outer surface of the cover 12 and is configured to slide between a first stop 16 and a second stop 18. The slide 14 slides into engagement with the first or second stops 16, 18 so as to generate an impacting force and retracting force, respectively. The first stop 16 is disposed on a proximal end of the instrument 10 and the second stop 18 is disposed on a distal end of the instrument 10. For clarity, the term distal end refers to the end of the instrument 10 which is furthest from the surgical site 700 and the proximal end refers to the end of the instrument opposite the distal end.

The instrument 10 is preferably formed of a durable and rigid material such as titanium. The outer surface of the cover 12 and the inner surface of the slide 14 may have a coating configured to facilitate sliding of the slide 14 along the outer surface of the cover 12. FIG. 2 is an illustration showing the handle 502 nested within the cover 12 of the instrument 10.

Figure 3:
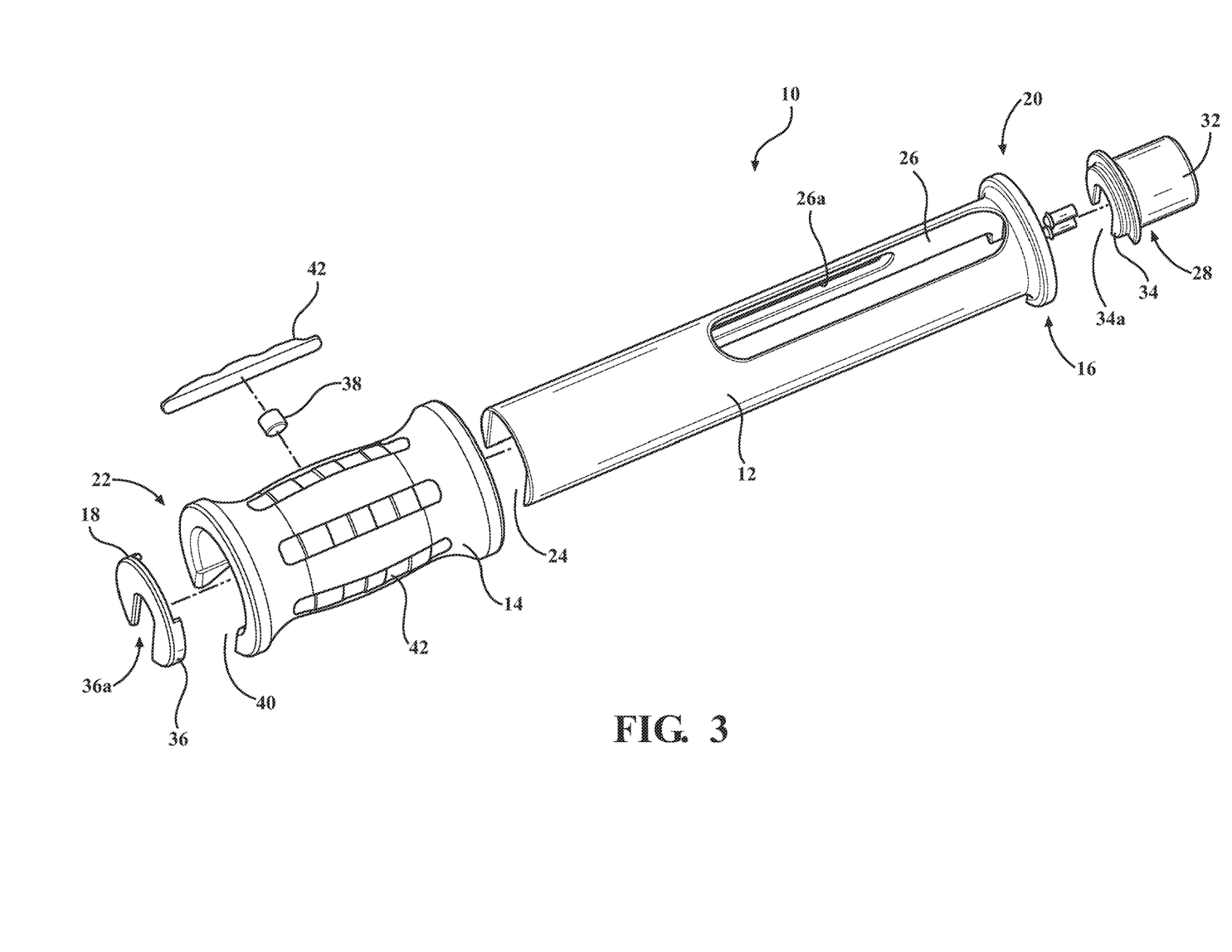
FIG. 3 is an exploded view of the instrument.
Figure 4:
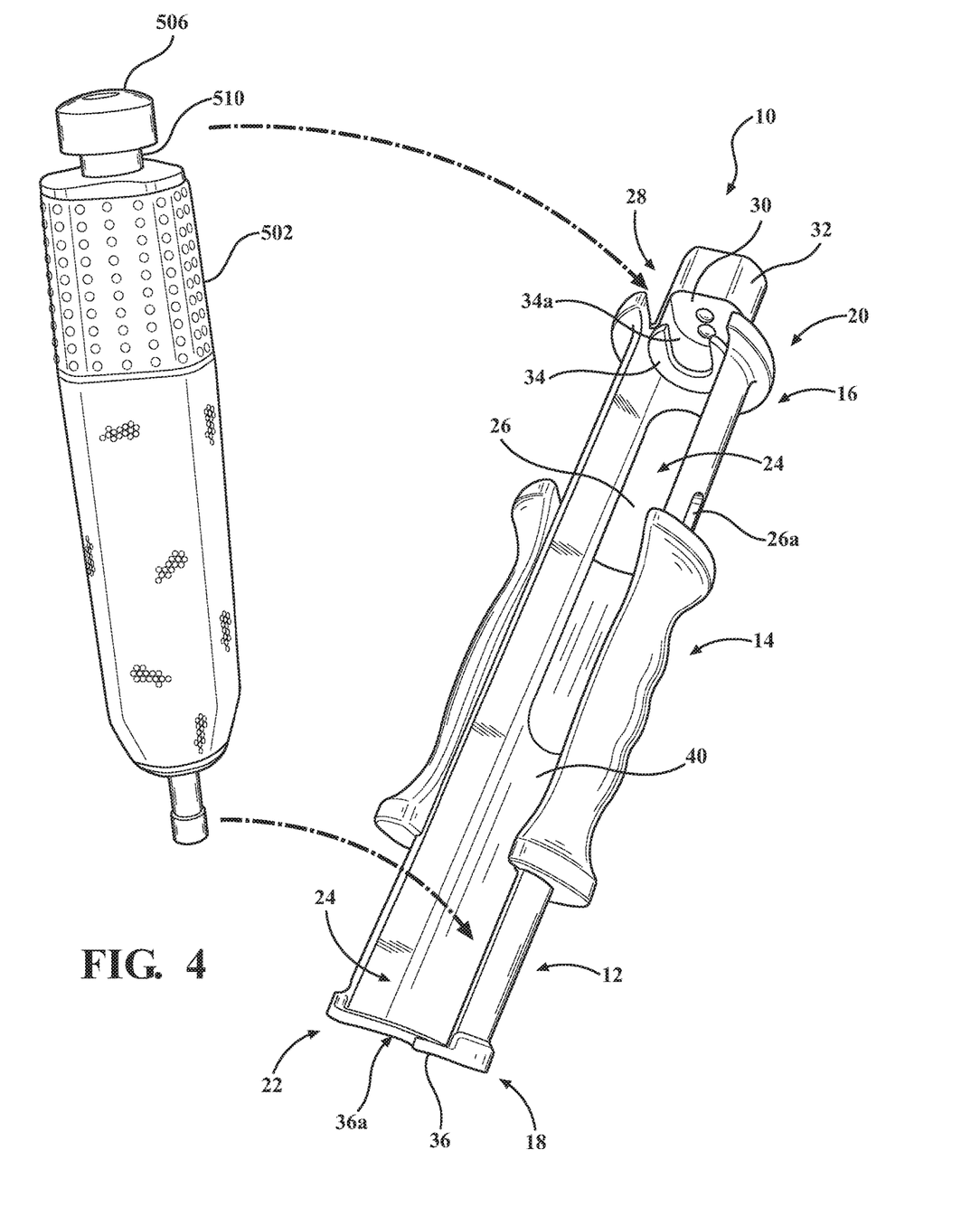
FIG. 4 is a perspective view of the handle of the inserter being inserted into the instrument.
Figure 5:
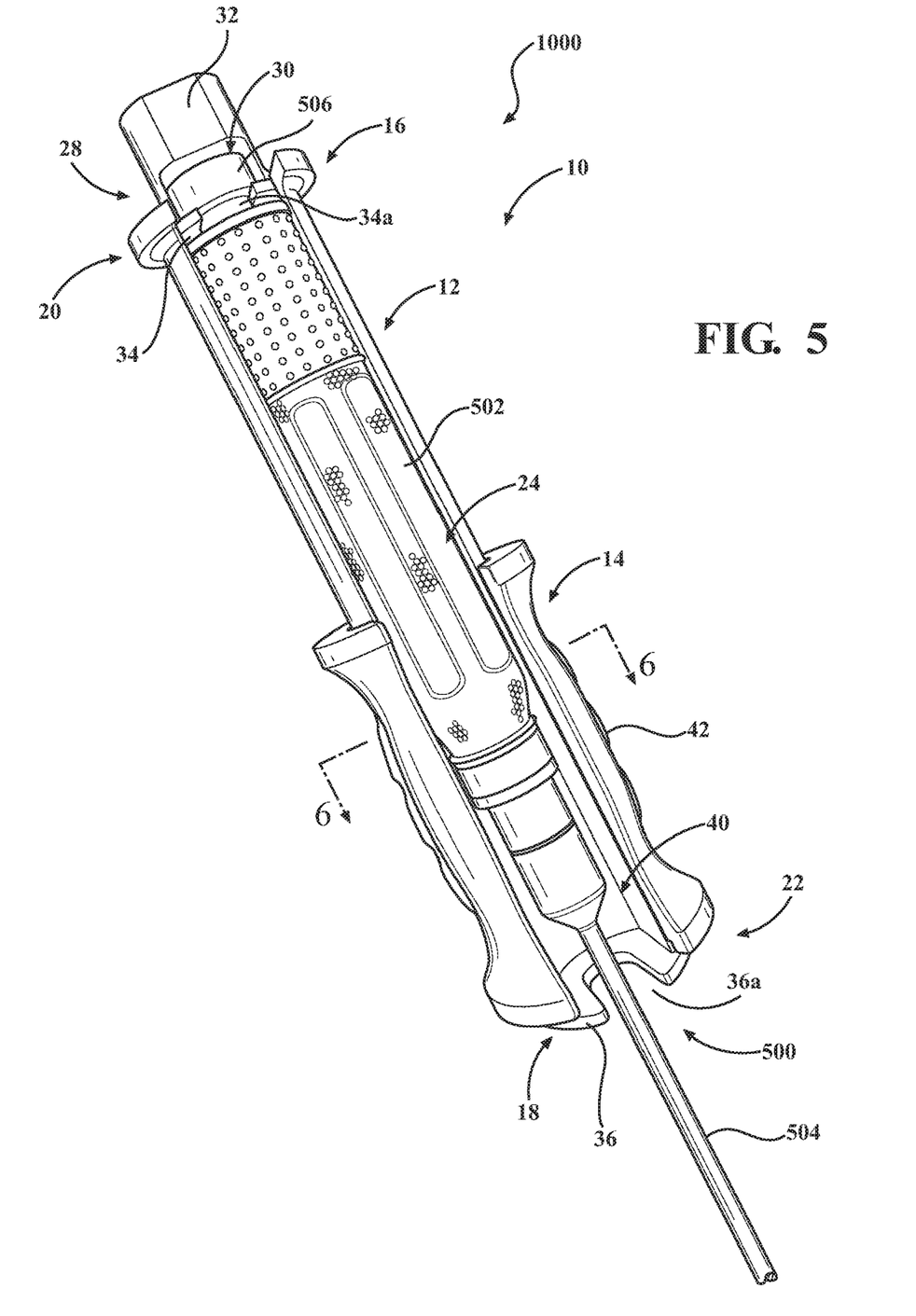
FIG. 5 is a perspective view of the instrument showing the slide engaged with a second radial lip.

With reference now to FIGS. 3-5, the cover 12 is adapted to be mounted onto the handle 502. FIG. 4 is a perspective view of the handle 502 separated from the instrument 10. The arrows illustrate how the handle 502 is seated within the cover 12. As shown, the cover 12 is a generally cylindrical member having a first closed end 20 opposite a second closed end 22 and a slot 24 extending between the first and second closed ends 20, 22. The first closed end 20 is disposed on a proximal end of the instrument 10 and the second closed end 22 is disposed on a distal end of the instrument 10. The slot 24 provides the cover 12 with a generally C-shaped cross section. The slot 24 is dimensioned so as to receive the handle 502 of the inserter 500.

The slide 14 is shown disposed along a mid-portion of the cover 12, i.e., positioned generally half-way between the first closed end 20 and second closed end 22, to illustrate how the slide 14 can move between the first and second closed ends 20, 22 of the cover 12. The cover 12 may include a pair of elongated openings 26. The elongated openings 26 may be useful in reducing the weight of the instrument 10 and to help facilitate cleaning of the interior of the cover 12.

The instrument 10 includes an engagement portion 28 disposed on the first closed end 20 of the cover 12. The first stop 16 may be integrally formed to the engagement portion 28 on the first closed end 20 of the cover 12. Alternatively, the first stop 16, the engagement portion 28 and the first closed end 20 may be separate parts.

In one embodiment, the engagement portion 28 is a pocket 30 defined by a block member 32 spaced apart from a C-shaped disk 34. The block member 32 may be formed of a rigid material configured to withstand the blow of a hammer. The pocket 30 is configured to engage the hammer support surface 506 of the handle 502. In one embodiment, the second closed end 22 of the cover 12 is a disk 36 having a U-shaped slot 36a configured to receive a portion of an inserting rod 504 of the inserter 500. Thus it should be appreciated that the entire handle 502 may be disposed and seated within an elongated seat defined by the cover 12.

With reference again to FIGS. 3 and 4, the slide 14 has an inner surface having a generally U-shaped profile which is complimentary to the outer surface of the cover 12. The disk 36 having a U-shaped slot 36a is illustratively shown as a part separate from the slide 14. A pin 38 may be mounted to the slide 14 and rides within the elongated opening 26a of the cover 12 so as to prevent the slide 14 from disengaging from the cover 12 and to prevent rotation of the slide relative to the cover 12 during movement of the slide 14 along the cover 12.

FIG. 5 is an illustrative view showing the instrument 10 mounted to an inserter 500. The hammer support surface 506 of the handle 502 is engaged in the engagement portion 28 of the instrument 10. FIG. 4 shows the hammer support surface 506 being spaced apart from a distal end of the handle 502 by a neck 510. The neck 510 may have an irregular shape wherein rotation of the neck 510 engages the inner edges of the U-shaped slot 34a of the disk 34 so as to help retain in a pinch fit engagement the handle 502 to the engagement portion 28 of the instrument 10.

FIG. 5 shows the slide 14 resting against the second stop 18. The second stop 18 may be integrally formed to the second closed end 22 of the cover 12. In one embodiment the second stop 18 is a second radial lip extending radially from the outer surface of the cover 12. Likewise, the first stop 16 is integrally formed to the first closed end 20 of the cover 12 and may be a first radial lip extending radially around the outer surface of the cover 12. The first and second stops 16, 18 work together with the slide 14 so as to provide an impacting force or retracting force to the inserter 500.

With reference again to FIGS. 2 and 5, an embodiment of the cover 12 is shown wherein the cover 12 is longer in length than the handle 502. Thus, the slide 14 may travel a distance greater than the length of the handle 502 so as to help generate an impacting force and retracting force. Further, it should be appreciated that lengthening the cover 12 does not increase the length of the inserter 500 as the length is added towards the distal end of the cover 12.

The slide 14 may be formed of a rigid and durable material. The slide 14 may be made larger in dimension, than what is shown in the figures so as to increase the weight of the slide 14 and thus increase the impacting force and retracting force of the instrument 10. The slide 14 has a generally C-shaped cross section wherein the ends of the slide 14 are flared with respect to the body. The center of the body may be rounded so as to have a general barrel shape.

With reference again to FIGS. 3-6, the slide 14 includes a slide slot 40 having a dimension similar to that of the slot 24 of the cover 12 so as to allow the handle 502 to be seated into the cover 12. The slide 14 may include gripping features 42 to help surgeons engage the slide 14. For illustrative purposes the gripping feature 42 is shown as a rubber material mounted along an outer surface of the slide 14. The rubber material is provided in the form of a strip having a plurality of detents to help facilitate the grip of a user. In one embodiment the slide 14 includes a pair of gripping features opposite each other.

Figure 6:
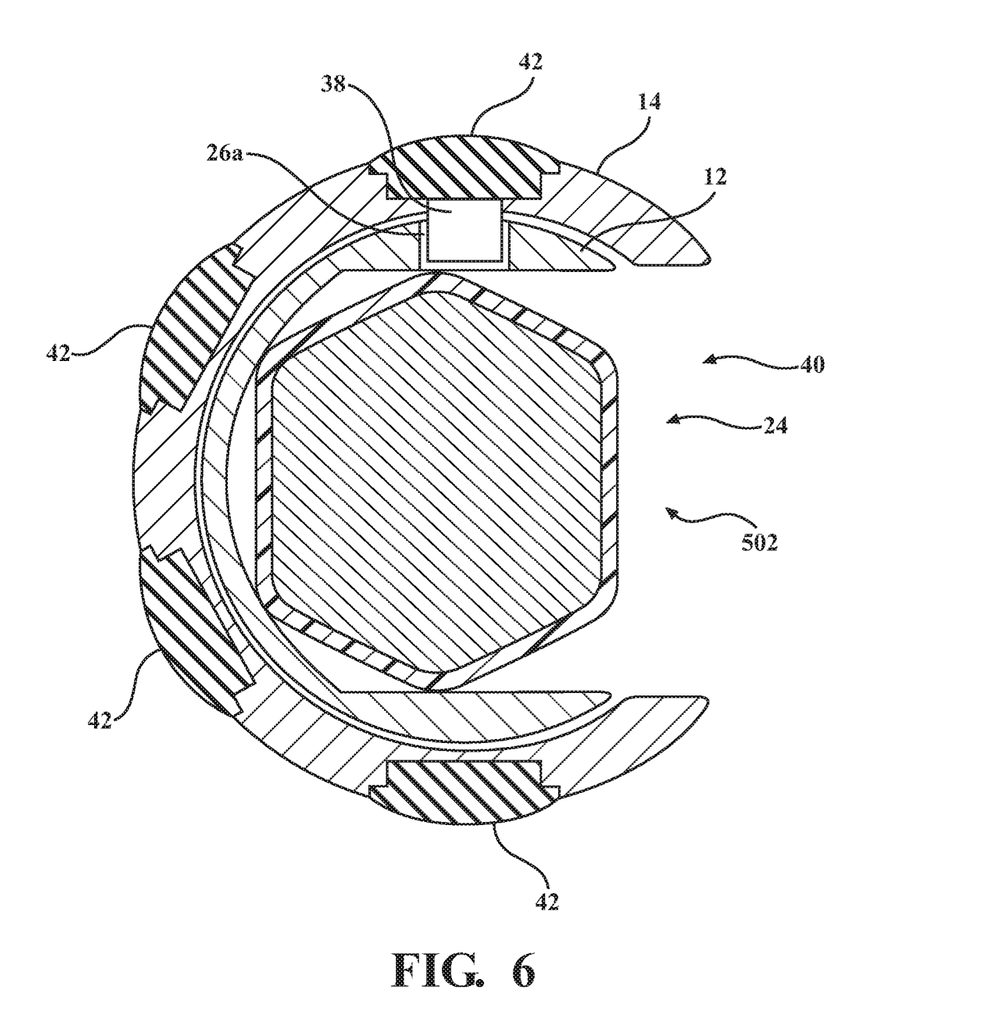
FIG. 6 is a cross-sectional view of the instrument and inserter shown in FIG. 5 taken along lines 6-6.
Figure 7:
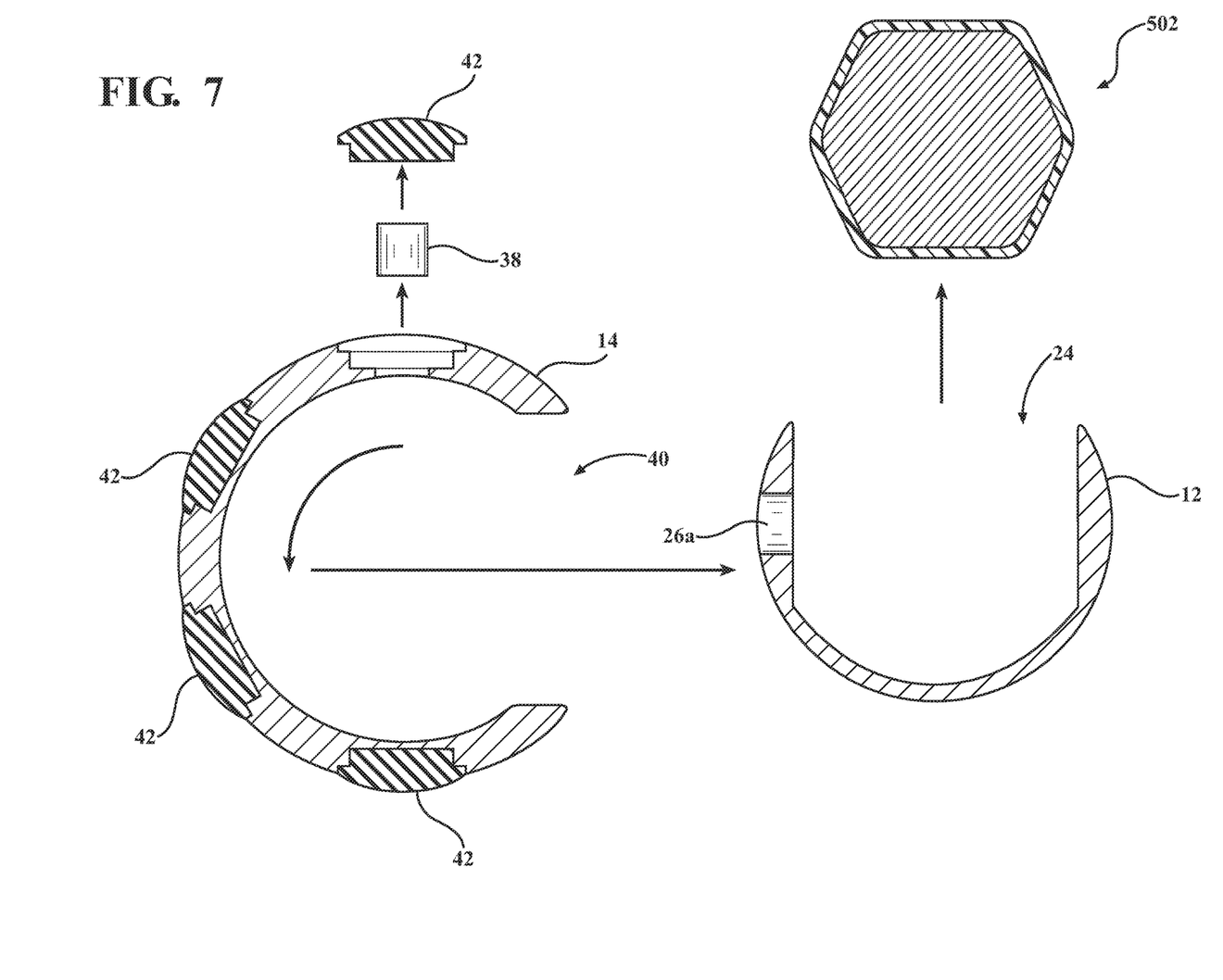
FIG. 7 is an exploded view of the instrument and handle shown in FIG. 6.

With reference now to FIGS. 5-7, the handle 502 may have an irregular shape as well. In particular, the handle 502 has a generally oblong cross section wherein the handle 502 is turned such that a narrow profile of the handle 502 is introduced into the slot 24 of the cover 12. The handle 502 may then be turned such that the wider profile of the handle 502 is seated within the cover 12 so as to provide a pinch fit engagement within the inner surface of the cover 12.

FIG. 6 provides a cross-sectional view of the instrument 12 mounted onto a handle 502. The handle 502 is shown having an irregular cross-section wherein the length between a front and back surface is shorter than the width of the handle 502. FIG. 6 shows the wider profile of the handle seated within the cover. For illustrative purposes, the handle 502 is shown as having a hexagonal shape, but it should be appreciated that the handle 502 may be shaped otherwise, such as, but not limited to, rectangular, oblong or the like.

FIG. 7 is an exploded view of FIG. 6 showing the assembly of the instrument 10. In particular, the slide 14 may be turned to receive the cover 12. The cover 12 is then rotated so as to align the slide slot 40 with the slot 24. The pin 38 may then be inserted into elongated slot 26a so as to retain the slide 14 with the cover 12.

With reference now to FIG. 2, an operation of the instrument 10 is provided. The instrument 10 is mounted onto a handle 502 so as to nest the handle 502 within the cover 12. The handle 502 is turned such that a narrow profile of the handle 502 is introduced into the slot 24 of the cover 12 and the side wherein the neck 510 between the hammer support surface 506 and distal end of the handle 502 is seated into the U-shaped slot 36 of the disk 34. The instrument 10 is then rotated generally 90 degrees so that the wide profile of the handle 502 is seated against the inner surface of the cover 12 wherein a pinch fit engagement between the outer surface of the handle 502 and the inner surface of the cover 12 is provided. Likewise, the neck 510 of the tool engagement structure and the U-shaped slot 36 of the disk 34 work in concert to help retain the cover 12 onto the handle 502. The U-shaped slot 36 supports the hammer support surface 506 so as to prevent the hammer support surface 506 from being passed through the disk and thereby hold the cover 12 in a fixed relationship with the handle 502.

FIG. 2 shows the working end of the inserter 500 in the process of implanting an implant 2000 between adjacent vertebrae. The arrows indicate the movement of the slide 14 along the axial length of the cover 12. In one mode of operation the user may simply lift the slide 14 up towards the first stop 16 and allow the slide 14 to drop and impact the second stop 18 wherein the weight of the slide 14 generates an impacting force to help drive the implant 2000 into the surgical site. It should be appreciated that the user may throw the slide 14 from the first stop 16 towards the second stop 18 to generate a larger impacting force.

Alternatively, the engagement portion 28 of the cover 12 may be used to absorb a load of a hammer strike in instances where more force is needed. In instances where the implant 2000 is driven too far into the surgical site, the surgeon may simply throw the slide 14 up into the first stop 16 generating a retracting force pulling the implant 2000 from the surgical site. Accordingly, the instrument 10 reduces the space required relative to previous slap hammers.

With reference again to FIGS. 2 and 5, an inserter kit 1000 is provided. The inserter kit 1000 is configured to insert and/or retract an implant 2000 into a surgical site. The inserter kit 1000 includes an inserter 500. The inserter 500 includes a handle 502 and an inserting rod 504. The handle 502 may include a hammer support surface 506 extending from the proximal end of the handle 502. The hammer support surface 506 may be integrally formed to the handle 502 and is configured to receive a blow from a hammer (not shown). For illustrative purposes, the instrument 10 is shown only mounted to the handle 502 of the inserter 500.

The inserter kit 1000 further includes an instrument 10 configured to receive the handle 502 and impart an impacting force or retracting force onto the inserter 500. The instrument 10 includes a cover 12. The cover 12 is adapted to receive the handle 502 of the inserter 500. A slide 14 is slidably mounted to the outer surface of the cover 12 and is configured to slide 14 between a first stop 16 and a second stop 18.

The cover 12 is a generally cylindrical member having a first closed end 20 opposite a second closed end 22 and a slot 24 extending between the first and second closed ends 20, 22. The slot 24 provides the cover 12 with a generally C-shaped cross section. The slot 24 is dimensioned so as to receive the handle 502 of the inserter 500.

The instrument 10 includes an engagement portion 28 disposed on the second closed end 22 of the cover 12. The first stop 16 may be integrally formed to the engagement portion 28 the second closed end 22 of the cover. Alternatively, the first stop 16, the engagement portion 28 and the second closed end 22 may be separate parts.

In one embodiment, the engagement portion 28 is a pocket 30 defined by a C-shaped disk spaced apart from a block member 32. The pocket 30 is configured to engage the hammer support surface 506 of the handle 502. In one embodiment, the second closed end 22 of the cover 12 is a disk 34 having a U-shaped slot 36 configured to receive a portion of an inserting rod 504 of the inserter 500. Thus it should be appreciated that the entire handle 502 may be disposed and seated within the elongated seat defined by the cover 12.

The hammer support surface 506 of the handle 502 is engaged in the engagement portion 28 of the instrument 10. The hammer support surface 506 is spaced apart from a distal end of the handle 502 by a neck 510. The neck 510 may have an irregular shape wherein rotation of the neck 510 engages the inner edges of the U-shaped slot 36 of the disk 34 so as to help retain in a pinch fit engagement the handle 502 to the engagement portion 28 of the instrument 10. Likewise, the handle 502 may have an irregular shape as well. In particular, the handle 502 has a generally oblong cross section wherein the handle 502 is turned such that a narrow profile of the handle 502 is introduced into the slot 24 of the cover 12. The handle 502 may then be turned such that the wider profile of the handle 502 is seated within the cover 12 so as to provide a pinch fit engagement within the inner surface of the cover 12.

FIGS. 4 and 5 provide an embodiment of the cover 12 wherein the cover 12 is longer in length than the handle 502. Thus, the slide 14 may travel a distance greater than the length of the handle 502 so as to help generate an impacting force or a retracting force. Accordingly, it should be appreciated that the length of the cover 12 shown herein is provided for illustrative purposes and may be shortened or lengthened based upon the amount of impact or retracting load desired. Likewise, the shape and dimension of the slide may be other than what is shown in the drawings so as to generate a desired impact and retracting load.

The slide 14 may include a slide slot 40 having a dimension similar to that of the slot 24 of the cover 12 so as to allow the handle 502 to be seated into the cover 12. The slide 14 may include gripping features 42 to help surgeons engage the slide 14. For illustrative purposes the gripping feature 42 is shown as a rubber material mounted along an outer surface of the slide 14. The rubber material is provided in the form of a strip having a plurality of detents to help facilitate the grip of a user. In one embodiment the slide 14 includes a pair of gripping features opposite each other.

While particular embodiments have been illustrated and described herein, it should be appreciated that various other changes and modifications may be made without departing from the spirit and scope of the subject matter. Moreover, although various aspects of the claimed subject matter have been described herein, such aspects need not be utilized in combination.

The invention claimed is:

1. An instrument for generating an impact and retracting load to an inserter, the inserter having a handle and an inserter rod, the instrument comprising:

a cover having a lumen adapted to receive the handle of the inserter, the cover having a first stop opposite a second stop, a slot extending along a length of the cover, wherein the handle is partially bounded by the cover; and a slide slidably mounted to an outer surface of the cover and configured to slide between the first stop and the second stop, the slide sliding into engagement with the first or second stops so as to generate an impacting force and a retracting force to the inserter.

2. The instrument as set forth in claim 1, wherein the cover is a generally cylindrical member having a first closed end opposite a second closed end and the slot extends between the first and second closed ends, the slot providing the cover with a generally C-shaped cross section.

3. The instrument as set forth in claim 2, further including an engagement portion disposed on the first closed end of the cover.

4. The instrument as set forth in claim 3, wherein the engagement portion is a pocket defined by a C-shaped disk spaced apart from a block member.

5. The instrument as set forth in claim 1, further including a pin, and wherein the cover includes an elongated opening, the pin configured to mount onto the slide and engage the elongated opening, the elongated opening and pin cooperating with each other to help prevent the slide from disengaging from the cover.

6. The instrument as set forth in claim 1, wherein the first stop is a first radial lip extending radially from the outer surface of the cover, and the second stop is a second radial lip extending radially around the outer surface of the cover.

7. The instrument as set forth in claim 1, wherein the slide includes a slide slot having a dimension similar to that of the slot of the cover.

8. The instrument as set forth in claim 1, wherein the slide includes a gripping feature.

9. An inserter kit for inserting and retracting an implant into a surgical site, the inserter kit comprising:
an inserter, the inserter having a handle and inserting rod;
an instrument having a cover, the cover adapted to receive the handle of the inserter so as to bound an outer surface of the handle, the cover having a first stop opposite a second stop, a slot extending along a length of the cover, wherein the handle is partially bounded by the cover;
a slide slidably mounted to an outer surface of the cover and configured to slide between the first stop and the second stop so as to slide along a length of the handle, the slide sliding into engagement with the first or second stops so as to generate an impacting force and retracting force to the inserter.

10. The inserter kit as set forth in claim 9, further including a pin, and wherein the cover includes an elongated opening, the pin configured to mount onto the slide and engage the elongated opening, the elongated opening and the pin cooperating with each other to help prevent the slide from disengaging from the cover.

11. The inserter kit as set forth in claim 9, wherein the cover is a generally cylindrical member having a first closed end opposite a second closed end and the slot extends between the first and second closed ends, the slot providing the cover with a generally C-shaped cross section.

12. The inserter kit as set forth in claim 11, further including an engagement portion disposed on the first closed end of the cover.

13. The inserter kit as set forth in claim 12, wherein the engagement portion is a pocket defined by a C-shaped disk spaced apart from a block member.

14. The inserter kit as set forth in claim 9, wherein the first stop is a first radial lip extending radially from the outer surface of the cover, and the second stop is a second radial lip extending radially around the outer surface of the cover.

15. The inserter kit as set forth in claim 9, wherein the slide includes a slide slot having a dimension similar to that of the slot of the cover.

16. The inserter kit as set forth in claim 9, wherein the slide includes a gripping feature.

17. The inserter kit as set forth in claim 9, wherein the inserter further includes a hammer support surface, and wherein the cover includes an engagement portion configured to engage the hammer support surface.

18. The inserter kit as set forth in claim 17, wherein the engagement portion is a pocket defined by a C-shaped disk spaced apart from a block member, the pocket is configured to engage the hammer support surface of the handle.

19. The inserter kit as set forth in claim 17, wherein the handle has a generally oblong cross section.

20. The inserter kit as set forth in claim 19, wherein the hammer support surface is spaced apart from a distal end of the handle by a neck, wherein a second closed end of the cover is a disk having a U-shaped slot, and wherein the neck has an irregular shape wherein rotation of the neck engages an inner edge of the U-shaped slot of the disk so as to help retain, in a pinch fit engagement, the handle to the engagement portion of the instrument.

21. An inserter kit for inserting and retracting an implant into a surgical site, the inserter kit comprising:
an inserter, the inserter having an inserting rod and a handle with a generally oblong cross section;
an instrument having a cover, the cover adapted to receive the handle of the inserter, the cover having a first stop opposite a second stop, a slot extending along a length of the cover, wherein the handle is partially bounded by the cover; and
a slide slidably mounted to an outer surface of the cover and configured to slide between the first stop and the second stop, the slide sliding into engagement with the first or second stops so as to generate an impacting force and retracting force to the inserter;
wherein the inserter includes a hammer support surface,
wherein the cover includes an engagement portion configured to engage the hammer support surface,
wherein the hammer support surface is spaced apart from a distal end of the handle by a neck,
wherein a second closed end of the cover is a disk having a U-shaped slot, and
wherein the neck has an irregular shape wherein rotation of the neck engages an inner edge of the U-shaped slot of the disk so as to help retain, in a pinch fit engagement, the handle to the engagement portion of the instrument.

* * * * *